(12) United States Patent
Dhanak et al.

(10) Patent No.: US 6,849,635 B2
(45) Date of Patent: Feb. 1, 2005

(54) SULFONAMIDES

(75) Inventors: Dashyant Dhanak, King of Prussia, PA (US); Timothy F. Gallagher, Collegeville, PA (US); Steven D. Knight, King of Prussia, PA (US); Stanley J. Schmidt, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/477,053

(22) PCT Filed: May 7, 2002

(86) PCT No.: PCT/US02/14407
§ 371 (c)(1),
(2), (4) Date: Nov. 7, 2003

(87) PCT Pub. No.: WO02/089785
PCT Pub. Date: Nov. 14, 2002

(65) Prior Publication Data
US 2004/0152893 A1 Aug. 5, 2004

Related U.S. Application Data
(60) Provisional application No. 60/289,317, filed on May 7, 2001.

(51) Int. Cl.$^7$ .................. A61K 31/18; A61K 31/38; A61K 31/275; A61K 31/506
(52) U.S. Cl. .................. 514/256; 514/445; 514/524; 514/603; 514/604; 544/333; 549/65; 558/413; 564/87; 564/89
(58) Field of Search ................. 514/256, 445, 514/524, 603, 604; 544/333; 549/65; 558/413; 564/87, 89

(56) References Cited

U.S. PATENT DOCUMENTS 6,103,766 A   8/2000  Romero et al. ............. 514/604

FOREIGN PATENT DOCUMENTS

WO          94/20467    *   9/1994

\* cited by examiner

Primary Examiner—Peter O'Sullivan
(74) Attorney, Agent, or Firm—Linda E. Hall; Stephen Venetianer; Charles M. Kinzig

(57) ABSTRACT

The present invention relates to sulfonamides, pharmaceutical compositions containing them, and their use as antagonists of urotensin II.

8 Claims, No Drawings

SULFONAMIDES

This application is a 371 of International Application PCT/US02/14407, filed 7 May 2002; which claims the benefit of U.S. Provisional Application No. 60/289,317, filed 7 May 2001.

FIELD OF THE INVENTION

The present invention relates to sulfonamides, pharmaceutical compositions containing them and their use as urotensin II antagonists

BACKGROUND OF THE INVENTION

The integrated control of cardiovascular homeostasis is achieved through a combination of both direct neuronal control and systemic neurohormonal activation. Although the resultant release of both contractile and relaxant factors is normally under stringent regulation, an aberration in this status quo can result in cardiohemodynamic dysfunction with pathological consequences.

The principal mammalian vasoactive factors that comprise this neurohumoral axis, namely angiotensin-II, endothelin-1, norepinephrine, all function via an interaction with specific G-protein coupled receptors (GPCR). Urotensin-II, represents a novel member of this neurohumoral axis.

In the fish, this peptide has significant hemodynamic and endocrine actions in diverse end-organ systems and tissues:

smooth muscle contraction
    both vascular and non-vascular in origin including smooth muscle preparations from the gastrointestinal tract and genitourinary tract. Both pressor and depressor activity has been described upon systemic administration of exogenous peptide
osmoregulation:
    effects which include the modulation of transepithelial ion ($Na^+$, $Cl^-$) transport.
    Although a diuretic effect has been described, such an effect is postulated to be secondary to direct renovascular effects (elevated GFR)
metabolism:
    urotensin-II influences prolactin secretion and exhibits a lipolytic effect in fish (activating triacylglycerol lipase resulting in the mobilization of non-esterified free fatty acids)
    (Pearson, et. al. *Proc. Natl. Acad. Sci.* (*U.S.A.*) 1980, 77, 5021;Conlon, et. al. *J. Exp. Zool.* 1996, 275, 226.)

In studies with human Urotensin-II it was found that it:

was an extremely potent and efficacious vasoconstrictor
exhibited sustained contractile activity that was extremely resistant to wash out
had detrimental effects on cardiac performance (myocardial contractility)

Human Urotensin-II was assessed for contractile activity in the rat-isolated aorta and was shown to be the most potent contractile agonist identified to date. Based on the in vitro pharmacology and in vivo hemodynamic profile of human Urotensin-II it plays a pathological role in cardiovascular diseases characterized by excessive or abnormal vasoconstriction and myocardial dysfunction. (Ames et. al. *Nature* 1999, 401, 282; Douglas & Ohlstein (2001). Trends Cardiovasc. Med., 10: in press).

Compounds that antagonize the Urotensin-II receptor may be useful in the treatment of congestive heart failure, stroke, ischemic heart disease (angina, myocardial ischemia), cardiac arrhythmia, hypertension (essential and pulmonary), COPD, fibrosis (e. g. pulmonary fibrosis), restenosis, atherosclerosis, dyslipidemia, asthma, (Hay DWP, Luttmann M A, Douglas S A: 2000, Br J Pharmacol: 131; 10–12) neurogenic inflammation and metabolic vasculopathies all of which are characterized by abnormal vasoconstriction and/or myocardial dysfunction. Urotensin antagonists may provide end organ protection in hypersensitive cohorts in addition to lowering blood pressure.

Since U-II and GPR14 are both expressed within the mammalian CNS (Ames et. al. *Nature* 1999, 401, 282), they also may be useful in the treatment of addiction, schizophrenia, cognitive disorders/Alzheimers disease, (Gartlon J. Psychopharmacology (Berl) 2001 June; 155(4) :426–33), impulsivity, anxiety, stress, depression, pain, migraine, neuromuscular function, parkinsons, movement disorders, sleep-wake cycle, and incentive motivation (Clark et al. *Brain Research* 923 (2001) 120–127.

Functional U-II receptors are expressed in rhabdomyosarcomas cell lines and therefore may have oncological indications. Urotensin may also be implicated in various metabolic diseases such as diabetes (Ames et. al. *Nature* 1999, 401, 282, Nothacker et al., *Nature Cell Biology* 1: 383–385, 1999) and in various gastrointestinal disorders, bone, cartilage, and joint disorders (e. g. arthritis and osteoporosis); and genito-urinary disorders. Therefore, these compounds may be useful for the prevention (treatment) of gastric reflux, gastric motility and ulcers, arthritis, osteoporosis and urinary incontinence.

SUMMARY OF THE INVENTION

In one aspect this invention provides for sulfonamides and pharmaceutical compositions containing them.

In a second aspect, this invention provides for the use of sulfonamides as antagonists of urotensin II, and as inhibitors of urotensin II.

In another aspect, this invention provides for the use of sulfonamides for treating conditions associated with urotensin II imbalance.

In yet another aspect, this invention provides for the use of sulfonamides for the treatment of congestive heart failure, stroke, ischemic heart disease (angina, myocardial ischemia), cardiac arrhythmia, hypertension (essential and pulmonary), renal disease (acute and chronic renal failure/ end stage renal disease) along with peripheral vascular disease (male erectile dysfunction, diabetic retinopathy, intermittent claudication/ischemic limb disease) and ischemic/hemorrhagic stroke, COPD, restenosis, asthma, neurogenic inflammation, migraine, metabolic vasculopathies, bone/cartilage/joint diseases, arthritis and other inflammatory diseases, fibrosis (e. g. pulmonary fibrosis), sepsis, atherosclerosis, dyslipidemia, addiction, schizophrenia, cognitive disorders/Alzheimers disease, impulsivity, anxiety, stress, depression, parkinsons, movement disorders, sleep-wake cycle, incentive motivation, pain, neuromuscular function, diabetes, gastric reflux, gastric motility disorders, ulcers and genitourinary diseases.

The urotensin antagonist may be administered alone or in conjunction with one or more other therapeutic agents, said agents being selected from the group consisting of endothelin receptor antagonists, angiotensin converting enzyme (ACE) inhibitors, A-II receptor antagonists, vasopeptidase inhibitors, diuretics, digoxin, and dual non-selective β-adrenoceptor and $α_1$-adrenoceptor antagonists.

Other aspects and advantages of the present invention are described further in the following detailed description of the preferred embodiments thereof.

DETAILED DESCRIPTION OF THE INVENTION

The present invention provides for compounds of Formula (I):

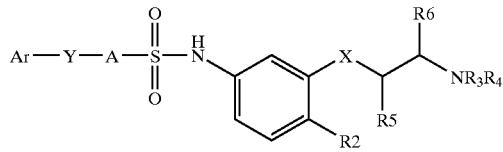

Formula (I)

wherein:

Ar is phenyl, thienyl, furanyl, pyridinyl, oxazoyl, pyrroyl, triazinyl, imidazoyl, pyrimidinyl, pyrazinyl, oxadiazoyl, pyrazoyl, triazoyl, thiazoyl, thiadiazoyl, quinolinyl, quinazolinyl, naphthyridinyl, azaspirononoyl, benzodioxanyl, benzodioxoyl, or benzodioxepinyl, substituted or unsubstituted by one, two, three or four of the following: halogen, CN, $S(C_{1-6}$ alkyl), $CF_3$, $OCF_3$, $SCF_3$, $C_{1-6}$ alkyl, $C_{1-6}$ alkoxy, $CO_2(C_{1-6}$ alkyl), $NR_9R_{10}$, $CONR_7R_8$, or $NO_2$;

A is phenyl, thienyl, furanyl, pyridinyl, oxazoyl, pyrroyl, triazinyl, imidazoyl, pyrimidinyl, pyrazinyl, N-phenylpyrroyl, oxadiazoyl, pyrazoyl, triazoyl, thiazoyl, thiadiazoyl, naphthyl, indoyl, quinolinyl, quinazolinyl, naphthyridinyl, benzothiophenyl, benzofuranyl, benzothiazoyl, benzoxazoyl, benzodioxanyl, benzodioxoyl, benzodioxepinyl, benzothiadiazoyl, benzoxadiazoyl, or benzimidazoyl, all of which may be substituted or unsubstituted by one, two, three or four halogens, $C_{1-6}$ alkyl, $C_{1-6}$ alkoxy, $CO_2(C_{1-6}$ alkyl), CN, or $CF_3$ groups;

Y is O, NH, $-S(O_n)-$, $CH_2$, or a bond;
$R_2$ is hydrogen, halogen, $CF_3$, CN, or $C_{1-4}$ alkyl;
$R_3$, $R_4$, $R_7$, and $R_8$ are independently hydrogen, $C_{1-6}$ alkyl, or benzyl;
$R_5$, $R_6$, $R_9$, and $R_{10}$ are independently hydrogen or $C_{1-6}$ alkyl;
X is O, S, or $CH_2$;
n is 0, 1, or 2;
or a pharmaceutically acceptable salt thereof.

When used herein, the term "alkyl" includes all straight chain and branched isomers. Representative examples thereof include methyl, ethyl, n-propyl, iso-propyl, n-butyl, sec-butyl, iso-butyl, t-butyl, n-pentyl and n-hexyl.

When used herein, the terms 'halogen' and 'halo' include fluorine, chlorine, bromine and iodine and fluoro, chloro, bromo and iodo, respectively.

The compounds of the present invention may contain one or more asymmetric carbon atoms and may exist in racemic and optically active form. All of these compounds and their diastereoisomers are contemplated to be within the scope of the present invention. Preferably Ar is phenyl which may be substituted or unsubstituted by halogen, CN, SMe, $YCF_3$, $C_{1-4}$ alkyl or $NO_2$.

Preferably Ar is phenyl, benzodioxoyl, or pyrimidinyl which may be substituted or unsubstituted by halogen, CN, $S(C_{1-6}$ alkyl), $CF_3$, $C_{1-6}$ alkyl, $C_{1-6}$ alkoxy, or $NO_2$.

Preferably A is phenyl or thienyl which may be substituted or unsubstituted by halogen, $C_{1-6}$ alkyl, or $C_{1-6}$ alkoxy.
Preferably Y is O, $-S(O_2)-$, or a bond.
Preferably $R_2$ is halogen or $CF_3$.
Preferably $R_3$ is $C_{1-6}$ alkyl; more preferably $R_3$ is methyl or ethyl.
Preferably $R_4$ is $C_{1-6}$ alkyl; more preferably $R_4$ is methyl or ethyl.
Preferably $R_5$ and $R_6$ are hydrogen.
Preferably X is O or $CH_2$.
Preferred Compounds are:

4-(3-Chloro-2-cyano-phenoxy)-N-[4-chloro-3-(2-dimethylamino-ethoxy)-phenyl]-benzenesulfonamide;
5-Benzenesulfonyl-thiophene-2-sulfonic acid [4-chloro-3-(2-dimethylamino-ethoxy)-phenyl]-amide;
3,5-Dichloro-N-[4-chloro-3-(2-dimethylamino-ethoxy)-phenyl]-4-(2-chloro-4-nitrophenoxy)-benzenesulfonamide;
5-(2-Methylsulfanyl-pyrimidin-4-yl)-thiophene-2-sulfonic acid [4-chloro-3-(2-dimethylamino-ethoxy)-phenyl]-amide;
N-[4-Chloro-3-(2-dimethylamino-ethoxy)-phenyl]-3-(4-chloro-phenoxy)-benzenesulfonamide;
N-[4-Chloro-3-(2-dimethylamino-ethoxy)-phenyl]-4-phenoxy-benzenesulfonamide;
N-[4-Chloro-3-(2-dimethylamino-ethoxy)-phenyl]-4-(4-methoxy-phenoxy)-benzenesulfonamide;
N-[4-Chloro-3-(2-dimethylamino-ethoxy)-phenyl]-4-(3,4-dichloro-phenoxy)-benzenesulfonamide;
N-[4-Chloro-3-(2-dimethylamino-ethoxy)-phenyl]-4-(2-chloro-phenoxy)-benzenesulfonamide;
N-[4-Chloro-3-(2-dimethylamino-ethoxy)-phenyl]-4-(2-methyl-phenoxy)-benzenesulfonamide;
N-[4-Chloro-3-(2-dimethylamino-ethoxy)-phenyl]-4-(2-trifluoromethyl-phenoxy)-benzenesulfonamide;
N-[4-Chloro-3-(2-dimethylamino-ethoxy)-phenyl]-4-(3,5-dichloro-phenoxy)-benzenesulfonamide;
N-[4-Chloro-3-(2-dimethylamino-ethoxy)-phenyl]-4-(3,4-dichloro-phenoxy)-benzenesulfonamide;
N-[4-Chloro-3-(2-dimethylamino-ethoxy)-phenyl]-3-(3,5-dichloro-phenoxy)-benzenesulfonamide;
2-Chloro-N-[4-chloro-3-(2-dimethylamino-ethoxy)-phenyl]-4-(2-cyano-3-chloro-phenoxy)-benzenesulfonamide;
2-Methyl-N-[4-chloro-3-(2-dimethylamino-ethoxy)-phenyl]-4-(2-cyano-3-chloro-phenoxy)-benzenesulfonamide;
2,6Dimethyl-N-[4-chloro-3-(2-dimethylamino-ethoxy)-phenyl]-4-(2-cyano-3-chloro-phenoxy)-benzenesulfonamide;
N-[4-Chloro-3-(2-dimethylamino-ethoxy)-phenyl]-4-(4-chloro-phenoxy)-benzenesulfonamide;
3,5-Dichloro-N-[4-chloro-3-(2-diethylamino-ethoxy)-phenyl]-4-(2-chloro-4-nitro-phenoxy)-benzenesulfonamide;
N-[4-Chloro-3-(2-dimethylamino-ethoxy)-phenyl]-4-(2-cyano-phenoxy)-benzenesulfonamide;
N-[4-Chloro-3-(2-dimethylamino-ethoxy)-phenyl]-4-(3-chloro-phenoxy)-benzenesulfonamide;
Biphenyl4-sulfonic acid [4-chloro-3-(2-dimethylamino-ethoxy)-phenyl]-amide;
4'-Chloro-biphenyl-4-sulfonic acid [4-chloro-3-(2-dimethylamino-ethoxy)-phenyl]-amide; 3',4'-Dichloro-biphenyl-4-sulfonic acid [4-chloro-3-(2-dimethylamino-ethoxy)-phenyl]-amide;
4-(3-Chloro-2-cyano-phenoxy)-N-[4-chloro-3-(2-diethylamino-ethoxy)-phenyl]-benzenesulfonamide hydrochloride;

2-methyl-5-methoxy-N-[4-chloro-3-(2-dimethylamino-ethoxy)-phenyl]-4-(2-cyano-3-chloro-phenoxy)-benzenesulfonamide;
4,5-Dimethoxy-biphenyl-2-sulfonic acid [4-chloro-3-(2-dimethylamino-ethoxy)-phenyl]-amide;
2-Benzo[1,3]dioxol-5-yl-N-[4-chloro-3-(2-dimethylamino-ethoxy)-phenyl]-4,5-dimethoxy-benzenesulfonamide;
4-(3-Chloro-2-cyano-phenoxy)-N-[4-chloro-3-(3-diethylamino-propyl)-phenyl]-benzenesulfonamide;
N-[4-Chloro-3-(2-dimethylamino-propoxy)-phenyl]-4-(3-chloro-2-methyl-phenoxy)-benzenesulfonamide;
4-(3-Chloro-2-cyano-phenoxy)-N-[4chloro-3-((S)-3-dimethylamino-but-2-oxy)-phenyl]-benzenesulfonamide;
4-(3-Chloro-2cyano-phenoxy)-N-[4-chloro-3-((R)-3-dimethylamino-but-2-oxy)-phenyl]-benzenesulfonamide; and
4-(3-Chloro-2-cyano-phenoxy)-N-[3-(2-dimethylamino-ethoxy)-4-trifluoromethyl-phenyl]-benzenesulfonamide.

More preferred compounds are:

4-(3-Chloro-2cyano-phenoxy)-N-[4chloro-3-(2-dimethylamino-ethoxy)-phenyl]-benzenesulfonamide;
4-(2-Chloro-4-nitro-phenoxy)-N-[4-chloro-3-(2-dimethylamino-ethoxy)-phenyl]-3,5-dichloro-benzenesulfonamide;
3-(3,5-Dichloro-phenoxy)-N-[4chloro-3-(2-dimethylamino-ethoxy)-phenyl]-benzenesulfonamide;
4-(2-Cyano-3-chloro-phenoxy)-N-[4-chloro-3-(2-dimethylamino-ethoxy)-phenyl]-2-chloro-benzenesulfonamide;
4-(2-Cyano-3-chloro-phenoxy)-N-[4-chloro-3-(2-dimethylamino-ethoxy)-phenyl]-2-methyl-benzenesulfonamide;
4-(2-Cyano-3-chloro-phenoxy)-N-[4-chloro-3-(2-dimethylamino-ethoxy)-phenyl]-2,6-dimethyl-benzenesulfonamide;
3-(3-Chloro-2-cyanophenoxy)-N-[3-(2-dimethylaminoethoxy)-4-trifluoromethylphenyl]-benzenesulfonamide; and
4-(3-Chloro-2-cyano-phenoxy)-N-[3-(2-dimethylamino-ethoxy)-4-trifluoromethyl-phenyl]-benzenesulfonamide.

Compounds of Formula (I) wherein X is oxygen, and $R_5$ and $R_6$ are hydrogen are prepared as outlined in Scheme 1.

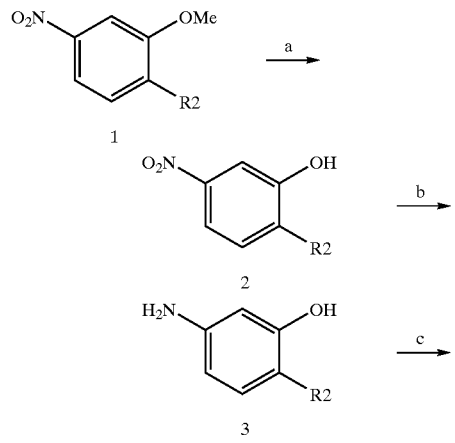

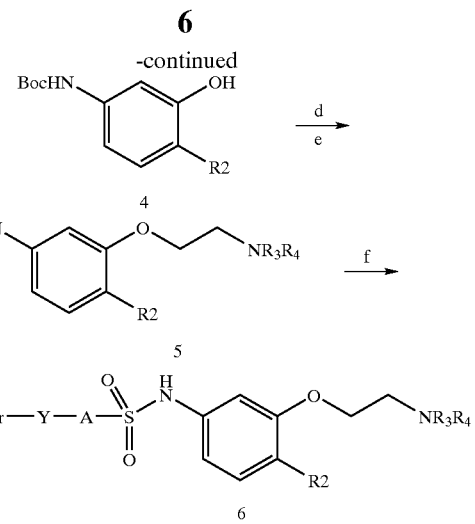

Conditions: a) 48% hydrogen bromide, acetic acid; b) hydrogen (50 psi), platinum on carbon, ethyl acetate; c) di-tert-butyldicarbonate, tetrahydrofuran, reflux; d) ClCH$_2$CH$_2$NR$_3$R$_4$-hydrochloride, potassium carbonate, water/1,2-dimethoxyethane, reflux; e) 6 N hydrogen chloride; f) Ar—Y-A-SO$_2$Cl, chloroform, ambient temperature. Ar, A, Y, $R_2$, $R_3$, and $R_4$ are as defined in Formula (I).

For example, acid-mediated demethylation of anisoles 1 gave phenols 2. Hydrogenation of the nitro group provided anilines 3, which were subsequently protected as their tert-butoxycarbonyl carbamates 4. Alkylation of 4 with various dialkylaminoethyl chlorides, followed by removal of the nitrogen protecting group afforded anilines 5. Subsequent sulfonylation of the anilines furnished the target compounds 6.

Preparation of Ar—Y-A-SO$_2$Cl that were not available commercially is set forth in scheme 2:

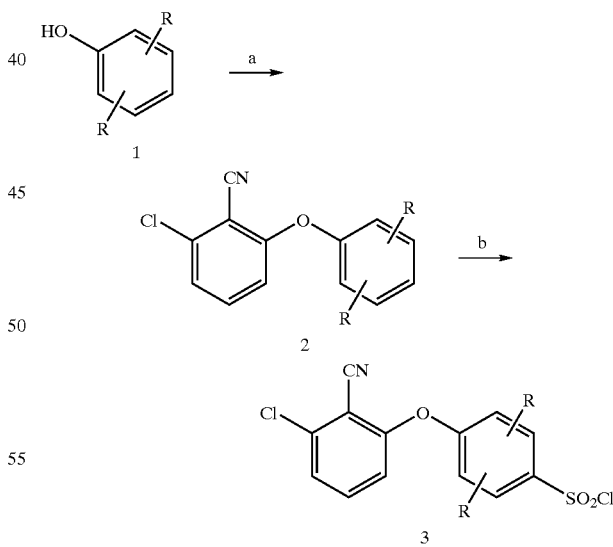

Conditions: a) Sodium hydride, dimethylsulfoxide; then 2,6-dichlorobenzonitrile, 100° C. ; b) chlorosulfonic acid, dichloromethane, 0° C. to ambient temperature. R is defined as halo, methyl, or methoxy.

Various phenols 1 were alkylated with 2,6-dichlorobenzonitrile to provide ethers 2. Treatment of 2 with chlorosulfonic acid furnished the desired sulfonyl chlorides 3.

Compounds wherein Y is a bond are prepared as set forth in scheme 3.

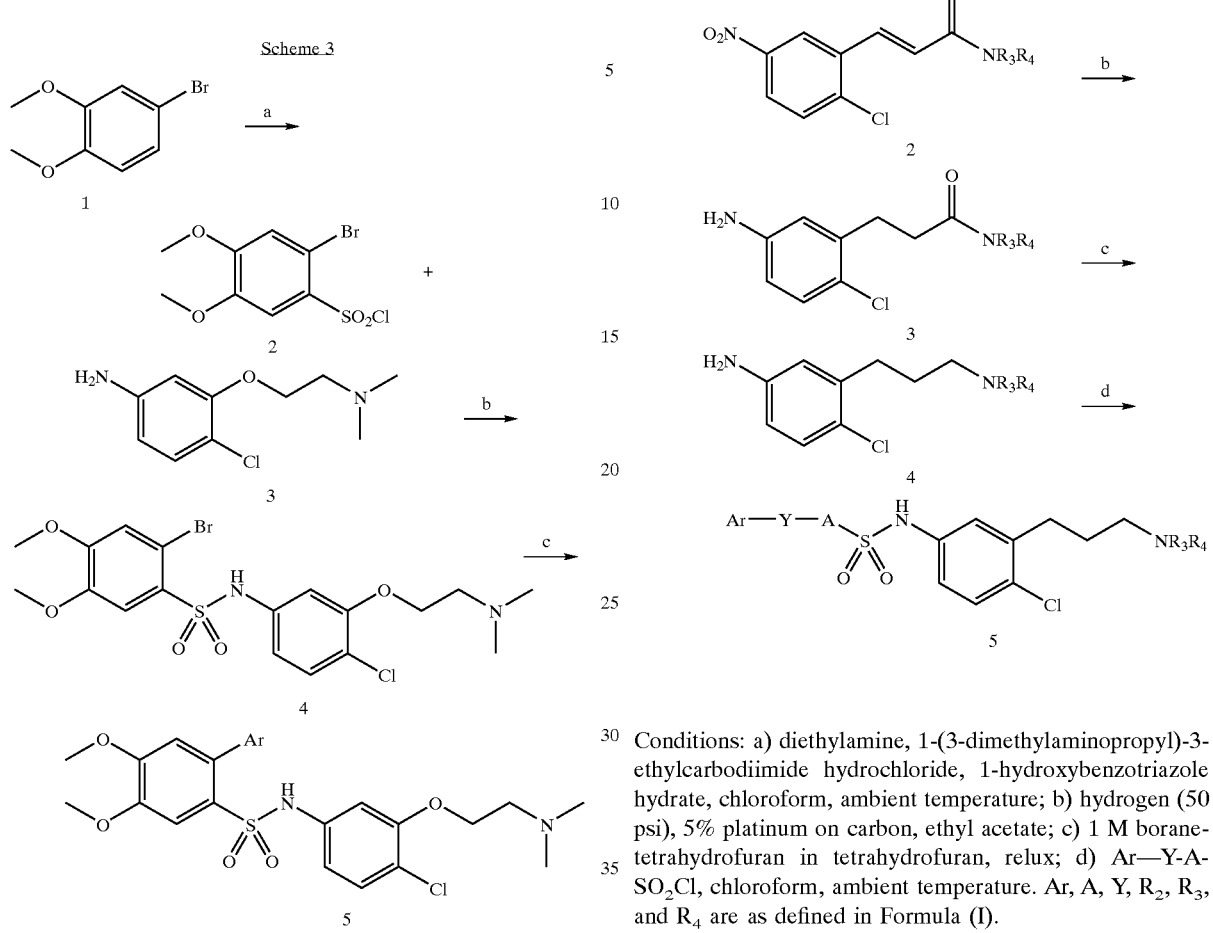

Conditions: a) chlorosulfonic acid, dichloromethane, 0° C. to ambient temperature; b) dichloroethane, ambient temperature; c) ArB(OH)$_2$, Pd(PPh$_3$)$_4$, cesium carbonate, 90° C. Ar is as defined I Formula (I).

Preparation of biphenyl analogs began by chlorosulfonation of 4-bromoveratrole (1) to give sulfonyl chloride 2. Coupling of 2 with aniline 3 at ambient temperature furnished sulfonamide 4. Palladium(0)-mediated Suzuki couplings using a range of arylboronic acids provided the desired biphenyl compounds 5.

Compounds wherein X is CH$_2$ are prepared as set forth in scheme 4:

Scheme 4

Conditions: a) diethylamine, 1-(3-dimethylaminopropyl)-3-ethylcarbodiimide hydrochloride, 1-hydroxybenzotriazole hydrate, chloroform, ambient temperature; b) hydrogen (50 psi), 5% platinum on carbon, ethyl acetate; c) 1 M borane-tetrahydrofuran in tetrahydrofuran, relux; d) Ar—Y-A-SO$_2$Cl, chloroform, ambient temperature. Ar, A, Y, R$_2$, R$_3$, and R$_4$ are as defined in Formula (I).

Preparation of analogs in which the dialylamino side chain is linked by an all carbon linker were derived from 2-chloro-5-nitrocinnamic acid (1). Coupling of 1 to various dialkylamines provided amides 2. Reductions of both the nitro groups and the side chain double bonds were accomplished with hydrogen (50 psi) and platinum on carbon to give anilines 3. Borane reductions of 3, followed by sulfonylations of the anilines furnished the desired sulfonamides 5.

Compounds wherein at least one of R$_5$ and R$_6$ is other than hydrogen are prepared as set forth in scheme 5:

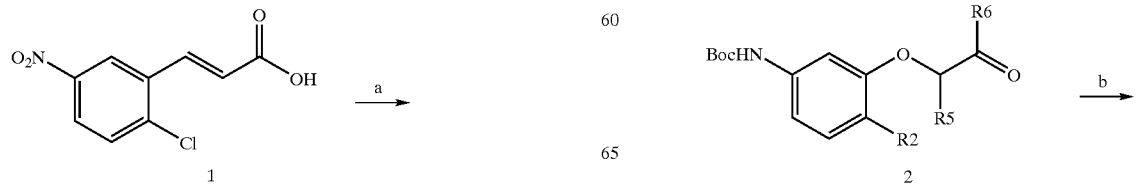

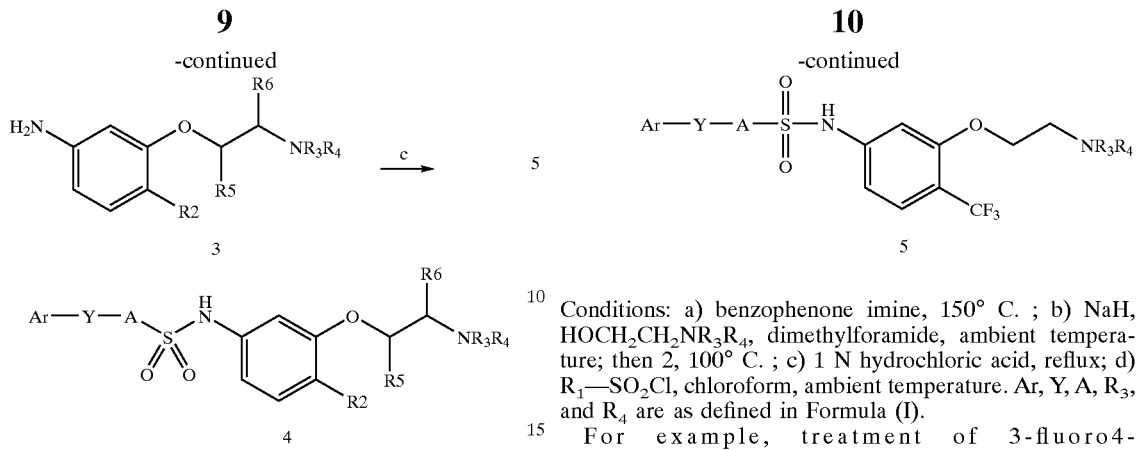

Conditions: a) $R_5CH(Cl)COR_6$, potassium carbonate, potassium iodide, acetone, reflux; b) $R_3R_4NH$-hydrochloride, methanol, sieves, reflux; then sodium cyanoborohydride; then 6 N hydrogen chloride, ambient temperature; c) Ar—Y-A-$SO_2Cl$, chloroform, ambient temperature. Ar, A, Y, $R_2$, $R_3$, and $R_4$ are as defined in Formula (I).

Alkylation of phenol 1 with various alpha-chloro-ketones provided 2. Reductive amination of the ketones 2 with various dialkylamines, followed by removal of the nitrogen protecting group gave anilines 3. Sulfonylations of 3 furnished the desired sulfonamides 4.

Compounds wherein $R_2$ is $CF_3$ may be prepared as follows:

Scheme 6

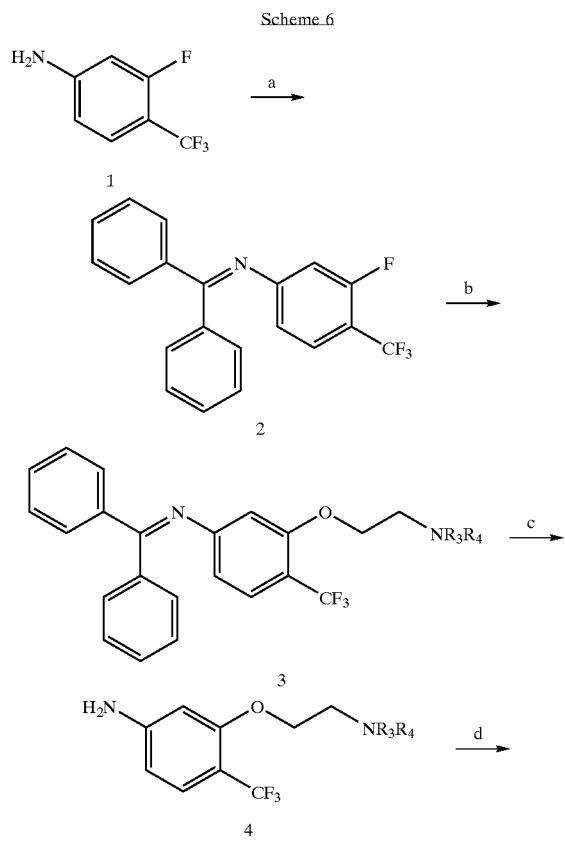

Conditions: a) benzophenone imine, 150° C. ; b) NaH, $HOCH_2CH_2NR_3R_4$, dimethylforamide, ambient temperature; then 2, 100° C. ; c) 1 N hydrochloric acid, reflux; d) $R_1$—$SO_2Cl$, chloroform, ambient temperature. Ar, Y, A, $R_3$, and $R_4$ are as defined in Formula (I).

For example, treatment of 3-fluoro4-trifluoromethylaniline (1) with benzophenone imine afford imine 2. Displacement of the fluoride was accomplished with various sodium alkoxides to provide ethers 3. Conversion of the imine back to the aniline, followed by sulfonylation with various sulfonyl chlorides furnished the desired sulfonamides 5.

In order to use a compound of the Formula (I) or a pharmaceutically acceptable salt thereof for the treatment of humans and other mammals it is normally formulated in accordance with standard pharmaceutical practice as a pharmaceutical composition.

Compounds of Formula (I) and their pharmaceutically acceptable salts may be administered in a standard manner for the treatment of the indicated diseases, for example orally, parenterally, sub-lingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (1) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1–400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 40 mg/Kg, of a compound of the Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

These sulphonamide analogs may be used for the treatment of congestive heart failure, stroke, ischemic heart disease (angina, myocardial ischemia), cardiac arrhythmia, hypertension (essential and pulmonary), renal disease (acute and chronic renal failure/end stage renal disease) along with peripheral vascular disease (male erectile dysfunction, diabetic retinopathy, intermittent claudication/ischemic limb disease) and ischemic/hemorrhagic stroke, COPD, restenosis, asthma, neurogenic inflammation, migraine, metabolic vasculopathies, bone/cartilage/joint diseases, arthritis and other inflammatory diseases, fibrosis (e.g. pulmonary fibrosis), sepsis, atherosclerosis, dyslipidemia, addiction, schizophrenia, cognitive disorders/Alzheimers disease, impulsivity, anxiety, stress, depression, pain, neuromuscular function, diabetes, gastric reflux, gastric motility disorders, ulcers and genitourinary diseases.

The urotensin antagonist may be administered alone or in conjunction with one or more other therapeutic agents, said agents being selected from the group consisting of endothelin receptor antagonists, angiotensin converting enzyme (ACE) inhibitors, A-II receptor antagonists, vasopeptidase inhibitors, diuretics, digoxin, and dual non-selective β-adrenoceptor and $\alpha_1$-adrenoceptor antagonists.

No unacceptable toxicological effects are expected when compounds of the invention are administered in accordance with the present invention.

The biological activity of the compounds of Formula (1) are demonstrated by the following tests:

Radioligand Binding:

HEK-293 cell membranes containing stable cloned human and rat GPR-14 (20 ug/assay) were incubated with 200 pM [125I] h-U-II (200 Ci/mmol$^{-1}$ in the presence of increasing concentrations of test compounds in DMSO (0.1 nM to 10 uM), in a final incubation volume of 200 ul (20 mM Tris-HCl, 5 mM MgCl2). Incubation was done for 30 minutes at room temperature followed by filtration GF/B filters with Brandel cell harvester. $^{125}$I labeled U-II binding was quantitated by gamma counting. Nonspecific binding was defined by $^{125}$I U-II binding in the presence of 100 nM of unlabeled human U-II. Analysis of the data was performed by nonlinear least square fitting.

Ca$^{2+}$-Mobilization:

A microtitre plate based Ca$^{2+}$-mobilization FLIPR assay (Molecular Devices, Sunnyvale, Calif.) was used for the functional identification of the ligand activating HEK-293 cells expressing (stable) recombinant GPR-14. The day following transfection, cells were plated in a poly-D-lysine coated 96 well black/clear plates. After 18–24 hours the media was aspirated and Fluo 3AM-loaded cells were exposed to various concentrations (10 nM to 30 uM) of test compounds followed by h-U-II. After initiation of the assay, fluorescence was read every second for one minute and then every 3 seconds for the following one minute. The inhibitory concentration at 50% (IC50)was calculated for various test compounds.

Inositol Phosphates Assays:

HEK-293-GPR14 cells in T150 flask were prelabeled overnight with 1 uCi myo-[$^3$H] inositol per ml of inositol free Dulbecco's modified Eagel's medium. After labeling, the cells were washed twice with Dulbecco's phosphate-buffered saline (DPBS) and then incubated in DPBS containing 10 mM LiCl for 10 min at 37° C. The experiment was initiated by the addition of increasing concentrations of h-U-II (1 pM to 1 $\mu$M) in the absence and presence of three different concentrations (0.3, 1 and 10 uM) of test compounds and the incubation continued for an additional 5 min at 37° C. after which the reaction was terminated by the addition of 10% (final concentration) trichloroacetic acid and centrifugation. The supernatants were neutralized with 100 ul of 1M Trizma base and the inositol phosphates were separated on AG 1-X8 columns (0.8 ml packed, 100–200 mesh) in formate phase. Inositol monophosphate was eluted with 8 ml of 200 mM ammonium formate. Combined inositol di and tris phosphate was eluted with 4 ml of 1M ammonium formate/0.1 M formic acid. Eluted fractions were counted in beta scintillation counter. Based on shift from the control curve $K_B$ was calculated.

Activity for the compounds of this invention range from (radioligand binding assay): Ki=50 nM-10000 nM (example 19 Ki=520 nM).

The following Examples are illustrative but not limiting embodiments of the present invention.

EXAMPLE 1

4-(3-Chloro-2-cyano-phenoxy)N-[4-chloro-3-(2-dimethylamino-ethoxy)-phenyl]-benzenesulfonamide.

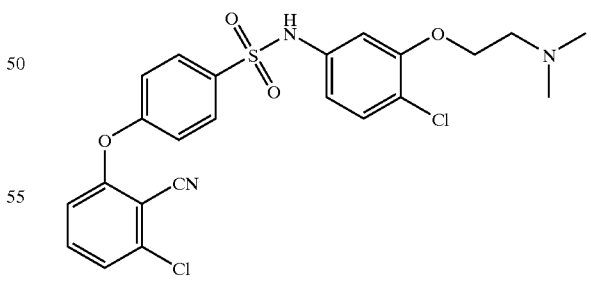

a). 2-Chloro-5-nitrophenol

2-Chloro-5-nitroanisole (310 g, 1.7 mol) was taken up in a mixture of 48% HBr (1.5 L) and AcOH (1.2 L) and heated at reflux for 3 days. The dark solution was allowed to cool to room temperature, poured into ice water (10 L), and let stand for 3 h. The resultant dull yellow solid was filtered, washed with water, and dried in vacuo (230 g, 79%): mp 115–117° C.

b). 2-Chloro-5-aminophenol

A solution of 2-chloro-5-nitrophenol (25 g, 0.14 mol) in ethyl acetate (150 mL) was treated with 5% Pt/C (250 mg) and the mixture shaken under a hydrogen atmosphere (30 psi) for 4 h. The mixture was filtered through Celite® and the residue washed well with hot ethyl acetate. The filtrate was treated with activated charcoal and re-filtered as above. Evaporation of the ethyl acetate gave a solid (19.8 g, 98%).

c). 4-Chloro-3-hydroxyphenylcarbamic acid tert-butyl ester

To a solution of 2-chloro-5-aminophenol (20 g, 0.14 mol) in THF (150 mL) was added a solution of di-tert-butyl dicarbonate (33 g, 0.15 mol) in THF (150 mL). The reaction was heated at reflux for 6 h, at which time it was allowed to cool to room temperature. The solvent was removed in vacuo and the residue diluted with ether (500 mL) and washed with 1 M citric acid (2×300 mL). The aqueous washings were extracted with ether (300 mL) and the combined organics washed with brine (300 mL), dried (MgSO$_4$), and concentrated. The resultant brown solid was triturated with hexanes and dried in vacuo to give 33 g (97%) of the title compound: mp 103–106° C.

d). 3-[2-(N,N-Dimethylamino)ethoxy]-4-chloroaniline

To a solution of 4-chloro-3-hydroxyphenylcarbamic acid tert-butyl ester (140 mg, 0.57 mmol) in 4:1 DME/water (5 mL) was added dimethylaminoethyl chloride hydrochloride (90 mg, 0.63 mmol) and K$_2$CO$_3$ (320 mg, 2.3 mmol). The reaction mixture was heated at reflux for 16 h, at which time it was allowed to cool to room temperature. The DME was removed in vacuo and the residue treated with 6 N HCl (2 mL). The resultant mixture was stirred at room temperature for 2 h, at which time it was diluted with water (5 mL) and washed with EtOAc (5 mL). The aqueous layer was basified with solid K$_2$CO$_3$ and extracted with EtOAc (2×10 mL). The EtOAc layers were washed with brine (10 mL), dried (MgSO$_4$), and concentrated to give 60 mg (50%) of the title compound.

e) 4-(3-Chloro-2-cyano-phenoxy)N-[4chloro-3-(2-dimethylamino-ethoxy)-phenyl]-benzenesulfonamide 3-[2-(N,N-Dimethylamino)ethoxy]-4-chloro-aniline (0.05 g, 0.23 mmol) was dissolved in CHCl$_3$ (0.5 mL). A solution of 4-(2-cyano-3-chloro-phenoxy)benzenesulfonyl chloride (0.076 g, 0.23 mmol) in CHCl$_3$ (0.5 mL) was added and the solution was allowed to shake for 5 days. The solution was evaporated and the residue purified by preparative reverse phase HPLC to give the title compound (0.05 g, 43%).

MS (ES+) m/e 506 [M+H]$^+$

Examples 2–18 were prepared as in Example I substituting the appropriate starting materials.

| Example | Compound | MS (ES+) m/e [M+H]$^+$ |
|---|---|---|
| 2 | 5-Benzenesulfonyl-thiophene-2-sulfonic acid [4-chloro-3-(2-dimethylamino-ethoxy)-phenyl]-amide | 501 |
| 3 | 3,5-Dichloro-N-[4-chloro-3-(2-dimethylamino-ethoxy)-phenyl]-4-(2-chloro-4-nitro-phenoxy)-benzenesulfonamide | 594 |

-continued

| Example | Compound | MS (ES+) m/e [M+H]+ |
|---|---|---|
| 4 | 5-(2-Methylsulfanyl-pyrimidin-4-yl)-thiophene-2-sulfonic acid [4-chloro-3-(2-dimethylamino-ethoxy)-phenyl]-amide | 485 |
| 5 | N-[4-chloro-3-(2-dimethylamino-ethoxy)-phenyl]-3-(4-chloro-phenoxy)-benzenesulfonamide | 481 |
| 6 | N-[4-chloro-3-(2-dimethylamino-ethoxy)-phenyl]-4-phenoxy-benzenesulfonamide | 447 |
| 7 | N-[4-chloro-3-(2-dimethylamino-ethoxy)-phenyl]-4-(4-methoxy-phenoxy)-benzenesulfonamide | 477 |

-continued
| Example | | Compound | MS (ES+) m/e [M+H]+ |
|---|---|---|---|
| 8 | 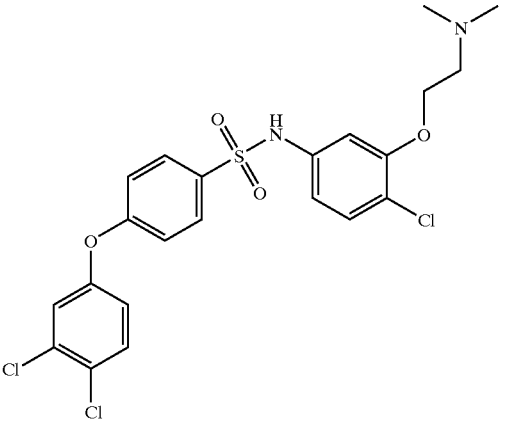 | N-[4-chloro-3-(2-dimethylamino-ethoxy)-phenyl]-4-(3,4-dichloro-phenoxy)-benzenesulfonamide | 515 |
| 9 | 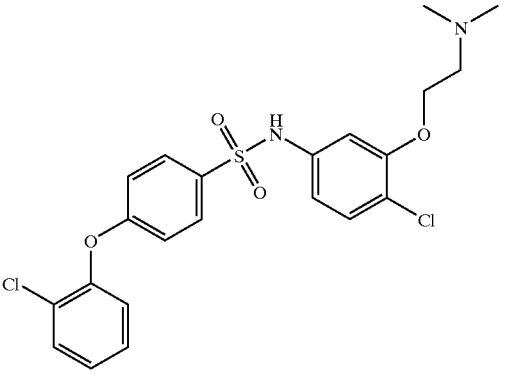 | N-[4-chloro-3-(2-dimethylamino-ethoxy)-phenyl]-4-(2-chloro-phenoxy)-benzenesulfonamide | 481 |
| 10 | 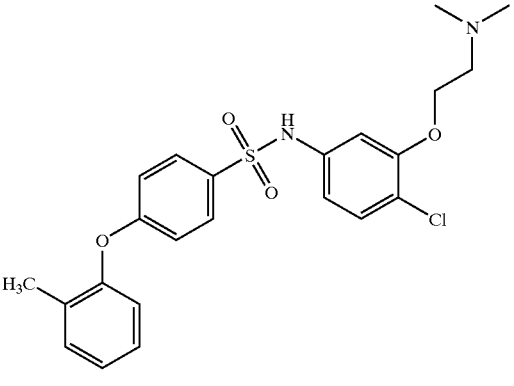 | N-[4-chloro-3-(2-dimethylamino-ethoxy)-phenyl]-4-(2-methyl-phenoxy)-benzenesulfonamide | 461 |

-continued

| Example | Compound | MS (ES+) m/e [M+H]+ |
|---|---|---|
| 11 | N-[4-chloro-3-(2-dimethylamino-ethoxy)-phenyl]-4-(2-trifluoromethyl-phenoxy)-benzenesulfonamide | 515 |
| 12 | N-[4-chloro-3-(2-dimethylamino-ethoxy)-phenyl]-4-(3,5-dichloro-phenoxy)-benzenesulfonamide | 515 |
| 13 | N-[4-chloro-3-(2-dimethylamino-ethoxy)-phenyl]-4-(3,4-dichloro-phenoxy)-benzenesulfonamide | 515 |

-continued

| Example | Compound | MS (ES+) m/e [M+H]+ |
|---|---|---|
| 14 | N-[4-chloro-3-(2-dimethylamino-ethoxy)-phenyl]-3-(3,5-dichloro-phenoxy)-benzenesulfonamide | 515 |
| 15 | 2-Chloro-N-[4-chloro-3-(2-dimethylamino-ethoxy)-phenyl]-4-(2-cyano-3-chloro-phenoxy)-benzenesulfonamide | 540 |
| 16 | 2-Methyl-N-[4-chloro-3-(2-dimethylamino-ethoxy)-phenyl]-4-(2-cyano-3-chloro-phenoxy)-benzenesulfonamide | 520 |
|  | 2,6-Dimethyl-N-[4-chloro-3-(2-dimethylamino-ethoxy)-phenyl]-4-(2-cyano-3-chloro-phenoxy)-benzenesulfonamide | 534 |

-continued

| Example | Compound | MS (ES+) m/e [M+H]+ |
|---|---|---|
| 17 | N-[4-Chloro-3-(2-dimethylamino-ethoxy)-phenyl]-4-(4-chloro-phenoxy)-benzenesulfonamide | 481 |
| 18 | 3,5-Dichloro-N-[4-chloro-3-(2-diethylamino-ethoxy)-phenyl]-4-(2-chloro-4-nitro-phenoxy)-benzenesulfonamide | 622 |
| 19 | N-[4-Chloro-3-(2-dimethylamino-ethoxy)-phenyl]-4-(2-cyano-phenoxy)-benzenesulfonamide | 472 |
| 20 | N-[4-Chloro-3-(2-dimethylamino-ethoxy)-phenyl]-4-(3-chloro-phenoxy)-benzenesulfonamide | 481 |
| 21 | Biphenyl-4-sulfonaic acid [4-chloro-3-(2-dimethylamino-ethoxy)-phenyl]-amide | 431 |
| 22 | | |

-continued

| Example | Compound | MS (ES+) m/e [M+H]+ |
|---|---|---|
| 23 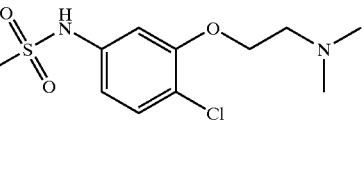 | 4'-Chloro-biphenyl-4-sulfonic acid [4-chloro-3-(2-dimethylamino-ethoxy)-phenyl]-amide | 465 |
| 24 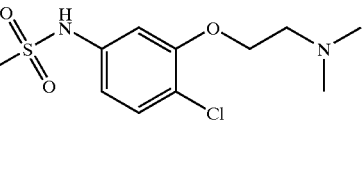 | 3',4'-Dichloro-biphenyl-4-sulfonic acid [4-chloro-3-(2-dimethylamino-ethoxy)-phenyl]-amide | 499 |
| 25 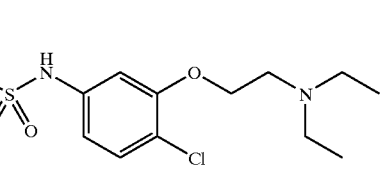 | 4-(3-Chloro-2-cyano-phenoxy)-N-[4-chloro-3-(2-diethylamino-ethoxy)-phenyl]-benzenesulfonamide hydrochloride | 534 |
| 26 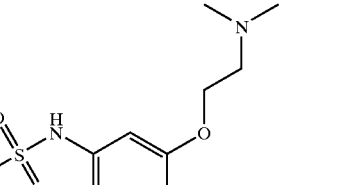 | 2-Methyl-5-methoxy-N-[4-chloro-3-(2-dimethylamino-ethoxy)-phenyl]-4-(2-cyano-3-chloro-phenoxy)-benzenesulfonamide | 550 |

EXAMPLE 16a 4-(3-Chloro-2-cyano-phenoxy)-2-methyl-benzenesulfonyl chloride

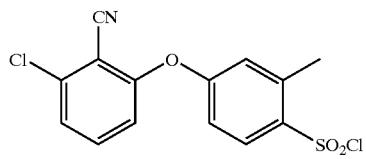

a) 2-Chloro-6-m-tolyloxybenzonitrile

To a suspension of sodium hydride (60% in oil, 550 mg, 14 mmol) in DMSO (15 mL) was added a solution of m-cresol (1.5 g, 14 mmol) in DMSO (15 mL). The reaction was stirred at ambient temperature for 15 minutes, at which time was added a solution of 2,6-dichlorobenzonitrile (2.3 g, 13 mmol) in DMSO (75 mL). The reaction was heated at 100° C. for 20 hours, allowed to cool to ambient temperature, and poured into water (500 mL). The resultant mixture was extracted with ethyl acetate (2×200 mL) and the combined extracts washed with 10% sodium hydroxide (300 mL) and water (300 mL), dried over magnesium sulfate, and concentrated to give 2-chloro-6-m-tolyloxybenzonitrile (2.4 g, 71%).

b) 4-(3-Chloro-2-cyano-phenoxy)-2-methyl-benzenesulfonyl chloride

To a cooled (0° C.) solution of 2-chloro-6-m-tolyloxybenzonitrile (1.1 g, 4.6 mmol) in dichloromethane (25 mL) was added dropwise chlorosufonic acid (0.46 mL, 7.0 mmol). The reaction was allowed to slowly warm to ambient temperature and maintained for 4 hours, at which time it was concentrated and diluted with ether (30 mL). The resultant solution was then washed with ice cold water (25 mL) and brine (25 mL), dried over magnesium sulfate, and concentrated to furnish a pale yellow oil (690 mg, 43%) which solidified upon standing.

Examples 16a, 18a and 19a were prepared as set forth in Example 17a substituting the appropriate starting materials.

maintained for 3 hours, at which time it was concentrated and diluted with ether (300 mL). The resultant solution was then washed with ice cold water (2×250 mL) and brine (100 mL), dried over magnesium sulfate, and concentrated to furnish a grayish powder (25 g, 78%).

b) 2-Bromo-N-[4-chloro-3-(2-dimethylamino-ethoxy)-phenyl]-4,5-dimethoxy-benzenesulfonamide To a solution of 3-[2-(N,N-dimethylamino)ethoxy]-4-chloroaniline (1.9 g, 8.8 mmol) in dichloroethane (50 mL) was added 2-bromo-3,4-dimethoxybenzenesulfonyl chloride (2.8 g, 8.8 mmol). The resultant solution was maintained at ambient temperature for 3 days, then concentrated. Crystallization from ethanol gave the title compound (3.4 g, 72%). MS (ES+) m/e 493 [M+H]$^+$

| Example | Compound |
|---|---|
| 15a | 4-(3-Chloro-2-cyano-phenoxy)-2-chloro-benzenesulfonyl chloride |
| 17a | 4-(3-Chloro-2-cyano-phenoxy)-2,6-dimethyl-benzenesulfonyl chloride |
| 26a | 4-(3-Chloro-2-cyano-phenoxy)-2-methyl-5-methoxy-benzenesulfonyl chloride |

EXAMPLE 27

4,5-Dimethoxy-biphenyl-2-sulfonic acid [4-chloro-3-(2-dimethylamino-ethoxy)-phenyl]-amide

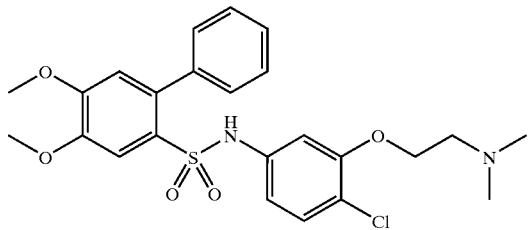

a) 2-Bromo-4,5-dimethoxybenzenesulfonyl chloride

To a cooled (0° C.) solution of 4-bromoveratrole (15 mL, 100 mmol) in dichloromethane (100 mL) was added dropwise chlorosufonic acid (26 mL, 400 mmol). The reaction was allowed to slowly warm to ambient temperature and c) 4,5-Dimethoxy-biphenyl-2-sulfonic acid [4-chloro-3-(2-dimethylamino-ethoxy)-phenyl]-amide To a solution of 2-bromo-N-[4-chloro-3-(2-dimethylamino-ethoxy)-phenyl]-4,5-dimethoxy-benzenesulfonamide (50 mg, 0.1 mmol) in dimethoxyethane/water (25:3, 2 mL) was added phenylboronic acid (120 mg, 1.0 mmol), cesium carbonate (820 mg, 2.5 mmol), and tetrakispalladium triphenylphosphine (6 mg, 0.005 mmol). The resultant mixture was heated at 90° C. for 16 hours, at which time it was diluted with ethyl acetate (10 mL) and washed with 5% sodium hydroxide (2×10 mL) and brine (10 mL). The solution was then dried over magnesium sulfate and concentrated to give a yellow oil. Purification by HPLC (gradient; 10% acetonitrile/water to 90% acetonitrile/water) furnished the title compound (15 mg, 31%) as a white solid. MS (ES+) m/e 491 [M+H]$^+$ Example 20 was prepared as outlined in Example 19, substituting the appropriate starting materials.

| Example | Compound | MS (ES+) m/e [M+H]+ |
|---|---|---|
| 28 | 2-Benzo[1,3]dioxol-5-yl-N-[4-chloro-3-(2-dimethylamino-ethoxy)-phenyl]-4,5-dimethoxy-benzenesulfonamide | 535 |

EXAMPLE 29

4-(Chloro-cyano-phenoxy)-N-[4-chloro-3-(3-diethylamino-propyl)-phenyl]-benzenesulfonamide

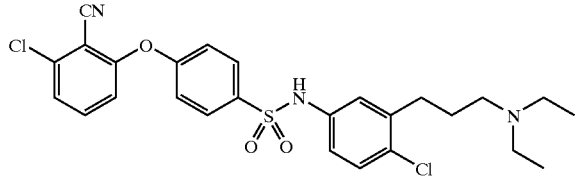

a) (E)-3-(5-Amino-2-chloro-phenyl)-N,N-diethylacrylamide

To a solution of 2-chloro-5-nitrocinnamic acid (10 g, 40 mmol) in chloroform (130 mL) was added diethylamine (5.5 mL, 50 mmol), 1-(3-dimethylaminopropyl)-3-ethylcarbodiimide hydrochloride (10 g, 50 mmol), and 1-hydroxybenzotriazole hydrate (7.1 g, 50 mmol). The reaction was stirred at ambient temperature for 4 days, at which time it was washed with saturated aqueous sodium bicarbonate (3×100 mL), 5% aqueous hydrogen chloride (3×100 mL), and brine (100 mL). The solution was then dried over magnesium sulfate and concentrated to give the title compound (12 g, 97%) as a white solid.

b) 3-(5-Amino-2-chloro-phenyl)-N,N-diethylpropionamide

To a solution of (E)-3-(5-amino-2-chloro-phenyl)-N,N-diethylacrylamide in ethyl acetate (50 mL) was added 5% platinum on carbon (1.5 g, 15 weight %). The resultant mixture was chraged with hydrogen (50 psi) and agitated for 20 hours, at which time it was filtered through Celite and concentrated to give the title compound (7.5 g, 83%) as a pale yellow oil. MS (ES+) m/e 255 [M+H]+ c) 4-Chloro-3-(3-diethylaminopropyl)-phenylamine

To a solution of 3-(5-amino-2-chloro-phenyl)-N,N-diethylpropionamide (3.6 g, 14 mmol) in tetrahydrofuran (50 mL) was added a solution of borane-tetrahydrofuran complex (1 M in tetrahydrofuran, 57 mL, 57 mmol). The resultant solution was heated at reflux for 24 hours, allowed to cool, and treated dropwise (over 15 minutes) with concentrated hydrochloric acid (4 mL) until solution became turbid. The mixture was stirred at ambient temperature for 1 hour, at which time it was concentrated. The residue was diluted with 10% aqueous sodium hydroxide (100 mL) and extracted with ethyl acetate (2×100 mL). The extracts were washed with brine (100 mL), dried over sodium sulfate, and concentrated to give the title compound (3.0 g, 88%) as a colorless oil. MS (ES+) m/e 241 [M+H]+ d) 4-(Chloro-cyano-phenoxy)-N-[4-chloro-3-(3-diethylamino-propyl)-phenyl]-benzenesulfonamide To a solution of 4-chloro-3-(3-diethylaminopropyl)-phenylamine (240 mg, 1.0 mmol) in chloroform (5 mL) was added 4-(3-chloro-2-cyano-phenoxy)-benzenesulfonyl chloride (330 mg, 1.0 mmol). The resultant solution was maintained at ambient temperature for 24 hours, at which time it was concentrated to give an oily residue. Purification of the residue by HPLC (gradient; 10% acetonitrile/water to 90% acetonitrile/water) furnished a yellow oil, which was subsequently dissolved in methanol (1 mL) and treated with 1 M hydrogen chloride in ether (1.5 mL) and stirred for 1 hour. Concentration of the mixture gave the title compound (69 mg, 13%) as a pale yellow solid. MS (ES+) m/e 521 [M+H]+

EXAMPLE 30

N-[4Chloro-3-(2-dimethylamino-propoxy)-phenyl]-4-(3-chloro-2-methyl-phenoxy-benzenesulfonamide

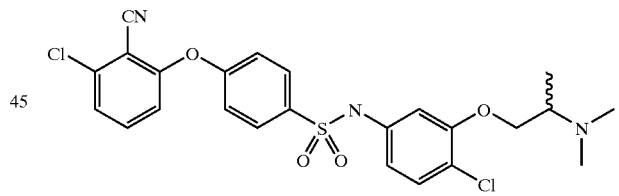

a) [4-Chloro-3-(2-oxo-propoxy)-phenyl]-carbamic acid tert-butyl ester

To a solution of (4-chloro-3-hydroxy-phenyl)-carbamic acid tert-butyl ester (240 mg, 1.0 mmol) and 1-chloropropan-2-one (220 mg, 2.0 mmol) in acetone (30 mL) was added potassium carbonate (340 mg, 2.0 mmol) and potassium iodide (16 mg, 0.1 mmol). The reaction mixture was heated at reflux for 16 hours, at which time it was concentrated. The resultant residue was diluted with water (20 mL) and extracted with ethyl acetate (2×20 mL). The combined organics were washed with brine (20 mL), dried over magnesium sulfate, and concentrated. Purification of the residue by flash chromatography (gradient; 10% ethyl acetate/hexanes to 20% ethyl acetate/hexanes) gave [4-chloro-3-(2-oxo-propoxy)-phenyl]-carbamic acid tert-butyl ester (210 mg, 70%).

b) 4-Chloro-3-(2-dimethylamino-propoxy)-phenylamine

To a solution of [4-chloro-3-(2-oxo-propoxy)-phenyl]-carbamic acid tert-butyl ester (500 mg, 1.6 mmol) in methanol (30 mL) was added dimethylamine hydrochloride (260 mg, 3.2 mmol) and 3 angstrom molecular sieves. The reaction mixture was heated at reflux for 16 hours, at which time it was allowed to cool and charged with sodium cyanoborohydride (200 mg, 3.2 mmol) and stirred at ambient temperature for 3 days. Methanol was removed via evaporation and the residue treated with 6 N hydrogen chloride (30 mL). The resultant mixture was stirred at ambient temperature for 4 hours, at which time it was diluted with water (50 mL) and washed with ether (50 mL). The aqueous layer was then basified with potassium hydroxide (until pH>10) and extracted with ether (2×50 mL). The combined organics were washed with water (50 mL) and brine (50 mL), dried over magnesium sulfate, and concentrated to furnish 4-chloro-3-(2-dimethylamino-propoxy)-phenylamine (120 mg, 50%). MS (ES+) m/e 229 [M+H]$^+$ c) N-[4-Chloro3-(2-dimethylamino-propoxy)-phenyl]-4-(3-chloro-2-methyl-phenoxy)-benzenesulfonamide To a solution of 4-chloro-3-(2-dimethylamino-propoxy)-phenylamine (100 mg, 0.5 mmol) in chloroform (10 mL) was added 4-(3-chloro-2-cyano-phenoxy)-benzenesulfonyl chloride (160 mg, 0.5 mmol). The resultant solution was maintained at ambient temperature for 24 hours, at which time it was concentrated to give an oily residue. Purification of the residue by flash chromatography (94:5:1-dichloromethane/methanol/ammonium hydroxide) furnished the title compound (26 mg, 10%) as a sticky yellow solid. MS (ES+) m/e 509 [M+H]$^+$ Examples 23 and 24 were prepared as set forth in Example 22, substituting the appropriate starting materials.

EXAMPLE 33

4-(3-chloro-2-cyano-phenoxy)-N-[3-(2-dimethylamino-ethoxy)-4-trifluoromethyl-phenyl]-benzenesulfonamide

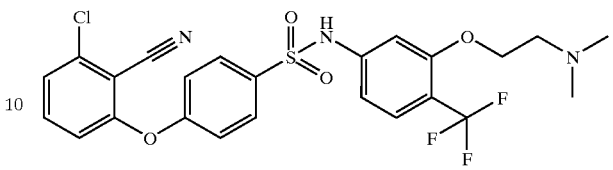

a) Benzhydrylidine-(3-fluoro-4-trifluoromethyl-phenyl)-amine.

A mixture of 4-amino-2-fluorobenzotrifluoride (5.0 g, 28 mmol) and benzophenone imine (4.7 mL, 5.1 g, 28 mmol) was heated at 150° C. for 3 h. After cooling to rt, the reaction mixture was vacuum filtered through a pad of silica gel eluting successively with hexanes, 4% and 10% EtOAc in hexanes to afford the title compound as a yellow oil; yield 3.5 g (36%): LCMS 344 (M$^+$+H)

b) 3-(2-dimethylamino-ethoxy)-4-trifluoromethyl-phenylamine

To a solution of 2-dimethylaminoethanol (0.65 g, 7.3 mmol) in DMF (73 mL) was added NaH (60% in mineral oil, 0.29 g, 7.3 mmol) at rt. The reaction mixture was stirrred at rt for 1 h and benzydrylidine-(3-fluoro-4-trifluoromethyl-phenyl)-amine (1.0 g, 2.9 mmol) was added. After heating at 100° C. for 3 h, the reaction mixture was cooled to rt and poured into sat'd. aq. NH$_4$Cl, extracted with EtOAc and the organic phase was concentrated under reduced pressure. The residue was treated with 1N HCl (100 mL) was heated at reflux for 0.5 h. The reaction mixture was cooled and

| Example | Compound | MS (ES+) m/e [M+H]$^+$ |
|---|---|---|
| 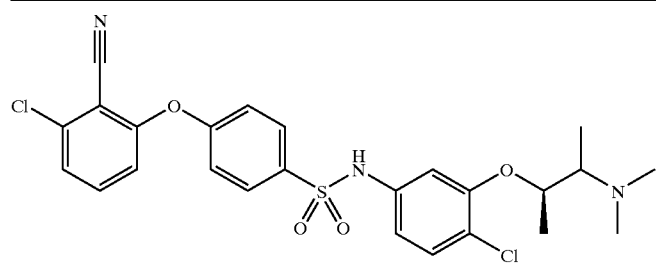 31 | 4-(3-Chloro-2-cyano-phenoxy)-N-[4-chloro-3-((S)-3-dimethylamino-but-2-oxy)-phenyl]-benzenesulfonamide | 534 |
| 32 | 4-(3-Chloro-2-cyano-phenoxy)-N-[4-chloro-3-((R)-3-dimethylamino-but-2-oxy)-phenyl]-benzenesulfonamide | 534 | extracted with ether. The aqueous phase was neutralized with 10% aq. NaOH and extracted with EtOAc. The organic phase was concentrated under reduced pressure to afford the title compound as a red oil; yield 0.25 g (35%): LCMS 249 ($M^+$+H).

c) 4-(3-chloro-2-cyano-phenoxy)-N-[3-(2-dimethylamino-ethoxy)-4-trifluoromethyl-phenyl]-benzenesulfonamide To a mixture of 3-(2-dimethylamino-ethoxy)-4-trifluoromethyl-phenylamine (0.10 g, 0.4 mmol) in $CHCl_3$ (2.5 mL) was added 4-(3-chloro-2-cyano-phenoxy) benzenesulfonyl chloride (0.13 g, 0.4 mmol) at rt. After stirring at rt for 72 h, the solvent was evaporated and the residue was purified by vacuum filtration through silica gel eluting successively with 4% MeOH in $CH_2Cl_2$ and 10% MeOH in $CH_2Cl_2$ followed by a mixture of $CH_2Cl_2$, MeOH and conc. $NH_4OH$ (90:10:1). The solvent was removed from the desired fractions and the residue was recrystallized from a mixture of MeOH and EtOAc to afford the title compound as a white solid; yield 0.01 g (5%): LCMS 540 ($M^+$+H).

EXAMPLE 34

Formulations for pharmaceutical use incorporating compounds of the present invention can be prepared in various forms and with numerous excipients. Examples of such formulations are given below.

| Tablets/Ingredients | Per Tablet |
|---|---|
| 1. Active ingredient (Cpd of Form. I) | 40 mg |
| 2. Corn Starch | 20 mg |
| 3. Alginic acid | 20 mg |
| 4. Sodium Alginate | 20 mg |
| 5. Mg stearate | 1.3 mg |
| | 2.3 mg |

Procedure for Tablets:

Step 1: Blend ingredients No. 1, No. 2, No. 3 and No. 4 in a suitable mixer/blender.

Step 2: Add sufficient water portion-wise to the blend from Step 1 with careful mixing after each addition. Such additions of water and mixing until the mass is of a consistency to permit its conversion to wet granules.

Step 3: The wet mass is converted to granules by passing it through an oscillating granulator using a No. 8 mesh (2.38 mm) screen.

Step 4: The wet granules are then dried in an oven at 140° F. (60° C.) until dry.

Step 5: The dry granules are lubricated with ingredient No. 5.

Step 6: The lubricated granules are compressed on a suitable tablet press.

Inhalant Formulation

A compound of Formula I, (1 mg to 100 mg) is aerosolized from a metered dose inhaler to deliver the desired amount of drug per use.

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then sterilized by filtration through a 0.22 micron membrane filter and sealed in sterile containers.

The above specification and Examples fully disclose how to make and use the compounds of the present invention. However, the present invention is not limited to the particular embodiments described hereinabove, but includes all modifications thereof within the scope of the following claims. The various references to journals, patents and other publications which are cited herein comprise the state of the art and are incorporated herein by reference as though fully set forth.

What is claimed is:

1. A compound of Formula (I):

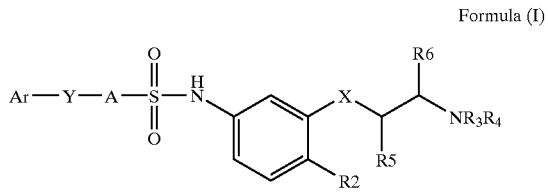

Formula (I)

wherein:

Ar is phenyl, thienyl, furanyl, pyridinyl, oxazoyl, pyrroyl, triazinyl, imidazoyl, pyrimidinyl, pyrazinyl, oxadiazoyl, pyrazoyl, triazoyl, thiazoyl, thiadiazoyl, quinolinyl, quinazolinyl, naphthyridinyl, azaspirononoyl, benzodioxanyl, benzodioxoyl, or benzodioxepinyl, substituted or unsubstituted by one, two, three or four of the following: halogen, CN, $S(C_{1-6}$ alkyl), $CF_3$, $OCF_3$, $SCF_3$, $C_{1-6}$ alkyl, $C_{1-6}$ alkoxy, $CO_2(C_{1-6}$ alkyl), $NR_9R_{10}$, $CONR_7R_8$, or $NO_2$;

A is phenyl, thienyl, furanyl, pyridinyl, oxazoyl, pyrroyl, triazinyl, imidazoyl, pyrimidinyl, pyrazinyl, N-phenylpyrroyl, oxadiazoyl, pyrazoyl, triazoyl, thiazoyl, thiadiazoyl, naphthyl, indoyl, quinolinyl, quinazolinyl, naphthyridinyl, benzothiophenyl, benzofuranyl, benzothiazoyl, benzoxazoyl, benzodioxanyl, benzodioxoyl, benzodioxepinyl, benzothiadiazoyl, benzoxadiazoyl, or benzimidazoyl, all of which may be substituted or unsubstituted by one, two, three or four halogens, $C_{1-6}$ alkyl, $C_{1-6}$ alkoxy, $CO_2(C_{1-6}$ alkyl), CN, or $CF_3$ groups;

Y is O, NH, —$S(O_n)$—, $CH_2$, or a bond;

$R_2$ is hydrogen, halogen, $CF_3$, CN, or $C_{1-4}$ alkyl;

$R_3$, $R_4$, $R_7$, and $R_8$ are independently hydrogen, $C_{1-6}$ alkyl, or benzyl;

$R_5$, $R_6$, $R_9$, and $R_{10}$ are independently hydrogen or $C_{1-6}$ alkyl;

X is O, S, or $CH_2$;

n is 0, 1, or 2;

or a pharmaceutically acceptable salt thereof.

2. A compound according to claim 1 wherein Ar is phenyl, benzodioxoyl, or pyrimidinyl which may be substituted or unsubstituted by halogen, CN, $S(C_{1-6}$ alkyl), $CF_3$, $C_{1-6}$ alkyl, $C_{1-6}$ alkoxy, or $NO_2$; A is phenyl or thienyl which may be substituted or unsubstituted by halogen, $C_{1-6}$ alkyl, or $C_{1-6}$ alkoxy; Y is O, —$S(O_2)$—, or a bond; $R_2$ is halogen or $CF_3$; $R_3$ is $C_{1-6}$ alkyl; $R_4$ is $C_{1-6}$ alkyl; $R_5$ and $R_6$ are hydrogen; $R_7$, $R_8$ $R_9$ and $R_{10}$ are hydrogen; and X is O or $CH_2$.

3. A compound according to claim 1 wherein Ar is phenyl which may be substituted or unsubstituted by halogen, CN, SMe, $YCF_3$, $C_{1-4}$ alkyl or $NO_2$; A is phenyl substituted or unsubstituted by halogen or methyl; $R_2$ is halogen; $R_3$ is methyl or ethyl; $R_4$ is methyl or ethyl; $R_5$ and $R_6$ are hydrogen; $R_7$, $R_8$ $R_9$ and $R_{10}$ are hydrogen; X is O; and Y is an O or a bond.

4. A compound according to claim 1 chosen from the group consisting of:

4-(3-Chloro-2-cyano-phenoxy)-N-[4-chloro-3-(2-dimethylamino-ethoxy)-phenyl]-benzenesulfonamide;

5-Benzenesulfonyl-thiophene-2-sulfonic acid [4-chloro-3-(2-dimethylamino-ethoxy)-phenyl]-amide;

3,5-Dichloro-N-[4-chloro-3-(2-dimethylamino-ethoxy)-phenyl]-4-(2-chloro-4-nitro-phenoxy)-benzenesulfonamide;

5-(2-Methylsulfanyl-pyrimidin-4-yl)-thiophene-2-sulfonic acid [4-chloro-3-(2-dimethylamino-ethoxy)-phenyl]-amide;

N-[4-chloro-3-(2-dimethylamino-ethoxy)-phenyl]-3-(4-chloro-phenoxy)-benzenesulfonamide;

N-[4-chloro-3-(2-dimethylamino-ethoxy)-phenyl]-4-phenoxy-benzenesulfonamide;

N-[4-chloro-3-(2-dimethylamino-ethoxy)-phenyl]-4-(4-methoxy-phenoxy)-benzenesulfonamide;

N-[4-chloro-3-(2-dimethylamino-ethoxy)-phenyl]-4-(3,4-dichloro-phenoxy)-benzenesulfonamide;

N-[4-chloro-3-(2-dimethylamino-ethoxy)-phenyl]-4-(2-chloro-phenoxy)-benzenesulfonamide;

N-[4-chloro-3-(2-dimethylamino-ethoxy)-phenyl]-4-(2-methyl-phenoxy)-benzenesulfonamide;

N-[4-chloro-3-(2-dimethylamino-ethoxy)-phenyl]-4-(2-trifluoromethyl-phenoxy)-benzenesulfonamide;

N-[4-chloro-3-(2-dimethylamino-ethoxy)-phenyl]-4-(3,5-dichloro-phenoxy)-benzenesulfonamide;

N-[4-chloro-3-(2-dimethylamino-ethoxy)-phenyl]-4-(3,4-dichloro-phenoxy)-benzenesulfonamide;

N-[4-chloro-3-(2-dimethylamino-ethoxy)-phenyl]-3-(3,5-dichloro-phenoxy)-benzenesulfonamide;

2-Chloro-N-[4-chloro-3-(2-dimethylamino-ethoxy)-phenyl]-4-(2-cyano-3-chloro-phenoxy)-benzenesulfonamide;

2-Methyl-N-[4-chloro-3-(2-dimethylamino-ethoxy)-phenyl]-4-(2-cyano-3-chloro-phenoxy)-benzenesulfonamide;

2,6-Dimethyl-N-[4-chloro-3-(2-dimethylamino-ethoxy)-phenyl]-4-(2-cyano-3-chloro-phenoxy)-benzenesulfonamide;

N-[4-Chloro-3-(2-dimethylamino-ethoxy)-phenyl]-4-(4-chloro-phenoxy)-benzenesulfonamide;

3,5-Dichloro-N-[4-chloro-3-(2-diethylamino-ethoxy)-phenyl]-4-(2-chloro-4-nitro-phenoxy)-benzenesulfonamide;

N-[4-Chloro-3-(2-dimethylamino-ethoxy)-phenyl]-4-(2-cyano-phenoxy)-benzenesulfonamide;

N-[4-Chloro-3-(2-dimethylamino-ethoxy)-phenyl]-4-(3-chloro-phenoxy)-benzenesulfonamide;

Biphenyl-4-sulfonic acid [4-chloro-3-(2-dimethylamino-ethoxy)-phenyl]-amide;

4'-Chloro-biphenyl-4-sulfonic acid [4-chloro-3-(2-dimethylamino-ethoxy)-phenyl]-amide;

3',4'-Dichloro-biphenyl-4-sulfonic acid [4-chloro-3-(2-dimethylamino-ethoxy)-phenyl]-amide;

4-(3-Chloro-2-cyano-phenoxy)-N-[4-chloro-3-(2-diethylamino-ethoxy)-phenyl]-benzenesulfonamide hydrochloride;

2-methyl-5-methoxy-N-[4-chloro-3-(2-dimethylamino-ethoxy)-phenyl]-4-(2-cyano-3-chloro-phenoxy)-benzenesulfonamide;

4,5-Dimethoxy-biphenyl-2-sulfonic acid [4-chloro-3-(2-dimethylamino-ethoxy)-phenyl]-amide;

2-Benzo[1,3]dioxol-5-yl-N-[4-chloro-3-(2-dimethylamino-ethoxy)-phenyl]-4,5-dimethoxy-benzenesulfonamide;

4-(Chloro-cyano-phenoxy)-N-[4-chloro-3-(3-diethylamino-propyl)-phenyl]-benzenesulfonamide;

N-[4-Chloro-3-(2-dimethylamino-propoxy)-phenyl]-4-(3-chloro-2-methyl-phenoxy)-benzenesulfonamide;

4-(3-Chloro-2-cyano-phenoxy)-N-[4-chloro-3-((S)-3-dimethylamino-but-2-oxy)-phenyl]-benzenesulfonamide;

4-(3-Chloro-2-cyano-phenoxy)-N-[4chloro-3-((R)-3-dimethylamino-but-2-oxy)-phenyl]-benzenesulfonamide; and 4-(3-chloro-2-cyano-phenoxy)-N-[3-(2-dimethylamino-ethoxy)-4-trifluoromethyl-phenyl]-benzenesulfonamide.

5. A compound according to claim 1 chosen from the group consisting of:

4-(3-Chloro-2-cyano-phenoxy)N-[4-chloro-3-(2-dimethylamino-ethoxy)-phenyl]-benzenesulfonamide;

4-(2-chloro-4-nitro-phenoxy)N-[4-chloro-3-(2-dimethylamino-ethoxy)-phenyl]-3,5-dichloro-benzenesulfonamide;

3-(3,5-Dichloro-phenoxy)N-[4-chloro-3-(2-dimethylamino-ethoxy)-phenyl]-benzenesulfonamide;

4-(2-cyano-3-chloro-phenoxy)N-[4-chloro-3-(2-dimethylamino-ethoxy)-phenyl]-2-chloro-benzenesulfonamide;

4-(2-cyano-3-chloro-phenoxy)N-[4-chloro-3-(2-dimethylamino-ethoxy)-phenyl]-2-methyl-benzenesulfonamide;

4-(2-cyano-3-chloro-phenoxy)N-[4-chloro-3-(2-dimethylamino-ethoxy)-phenyl]-2,6-dimethyl-benzenesulfonamide; and 4-(3-chloro-2-cyano-phenoxy)-N-[3-(2-dimethylamino-ethoxy)-4-trifluoromethyl-phenyl]-benzenesulfonamide.

6. A pharmaceutical composition comprising a compound of formula (I) of claim 1 and a pharmaceutically acceptable carrier or excipient.

7. A method of treating conditions associated with Urotensin-II imbalance by antagonizing the Urotensin-II receptor which comprises administering to a patient in need thereof, a compound of Formula I of claim 1.

8. A method according to claim 7 wherein the disease is congestive heart failure, stroke, ischemic heart disease, angina, myocardial ischemia, cardiac arrhythmia, essential and pulmonary hypertension, renal disease, acute and chronic renal failure, end stage renal disease, peripheral vascular disease, male erectile dysfunction, diabetic retinopathy, intermittent claudication/ischemic limb disease, ischemic/hemorrhagic stroke, COPD, restenosis, asthma, neurogenic inflammation, migraine, metabolic vasculopathies, bone/cartilage/joint diseases, arthritis and other inflammatory diseases, fibrosis, pulmonary fibrosis, sepsis, atherosclerosis, dyslipidemia, addiction, schizophrenia, cognitive disorders, Alzheimers disease, impulsivity, anxiety, stress, depression, parkinsons, movement disorders, sleep-wake cycle, incentive motivation, pain, neuromuscular function, diabetes, gastric reflux, gastric motility disorders, ulcers and genitourinary diseases.

* * * * *